United States Patent [19]

Razdan et al.

[11] 4,126,694
[45] Nov. 21, 1978

[54] COMPOSITION AND METHOD FOR TREATING GLAUCOMA

[75] Inventors: Raj K. Razdan, Belmont; Haldean C. Dalzell, Weston; Harry G. Pars, Lexington, all of Mass.

[73] Assignee: SISA Incorporated, Cambridge, Mass.

[21] Appl. No.: 762,832

[22] Filed: Jan. 27, 1977

[51] Int. Cl.$^2$ ............................................ A61K 31/35
[52] U.S. Cl. .................................................. 424/283
[58] Field of Search ......................................... 424/283

[56]     References Cited
U.S. PATENT DOCUMENTS

| | | | |
|---|---|---|---|
| 3,668,224 | 6/1972 | Petrzilka | 424/283 |
| 3,728,360 | 4/1973 | Pars et al. | 260/345.3 |
| 3,734,930 | 5/1973 | Razdan et al. | 424/283 |
| 3,799,946 | 3/1974 | Loev | 424/283 |
| 3,920,809 | 11/1975 | Thakkar | 424/283 |
| 4,025,536 | 5/1977 | Korte et al. | 424/283 |

OTHER PUBLICATIONS

Ophthalmologica 168, 366–369 (1974) D. Shapiro . . . The Ocular Manifestations of the Cannabinols . . .
Newsweek, Nov. 8, 1976, Pot and Glaucoma.
Chem. Abst. 83 158,044(r) (1975)–Purnell et al. "$\Delta^9$–Tetrahydrocannabinol . . . in Man".
Chem. Abst. 84 130,270(h) (1976) Green et al., "Interaction of Tetrahydrocannabinol in the Eye".

Primary Examiner—Albert T. Meyers
Assistant Examiner—D. W. Robinson

[57]            ABSTRACT

Tetrahydrodibenzopyrans having the structure

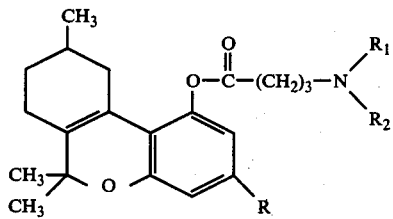

in which R, $R_1$, and $R_2$ are alkyl having from 1 to 4 carbon atoms and ophthalmologically acceptable acid addition salts thereof are effective anti-glaucoma agents, free from all but a very small amount of CNS activity, when applied topically.

4 Claims, No Drawings

COMPOSITION AND METHOD FOR TREATING GLAUCOMA

This invention relates to the treatment of glaucoma, particularly wide-angle glaucoma, by topical application to the eye of a therapeutic composition consisting essentially of an ophthalmologically acceptable topical carrier and an effective amount of a compound having the structure

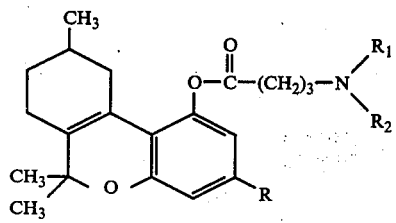

in which R, $R_1$ and $R_2$ are alkyl having from 1 to 4 carbon atoms and ophthalmologically acceptable acid addition salts thereof.

It has previously been reported that marijuana, $\Delta^9$-tetrahydrocannabinol and several benzopyranopyridines related to cannabinoids cause a fall in intraocular pressure, as stated in Pharmacology of Marijuana, Braude and Szara, (Raven, New York, 1976) pages 803–832, and in The Therapeutic Potential of Marijuana, Cohen and Stillman, (Plenum Press, New York, 1976). However, such compounds possess strong central nervous system (CNS) activity, in addition to having anti-glaucoma activity, and are therefore undesirable for use as therapeutic agents. Similarly, Pars et al. U.S. Pat. No. 3,728,360 teaches that various compounds which are dialkylamino esters of tetrahydrodibenzopyrans possess strong CNS activity.

The dialkylamino esters of tetrahydrodibenzopyrans of the present invention have very little CNS activity; tests in mice show the compounds to have much less CNS activity than $\Delta^9$-tetrahydrocannabinol.

It has now been found that tetrahydrodibenzopyrans having the structure defined in (I) above, although having little or no CNS activity, nevertheless possess effective anti-glaucoma activity in warm-blooded animals when applied topically to the eye. Application of the compound, preferably in a suitable topical carrier, to a single eye of a warm-blooded animal causes reduction of intraocular pressure in both eyes of the same animal.

The tetrahydrodibenzopyrans useful in the present invention can be prepared in the form of their hydrochloride salts by reacting 4-dialkylaminobutyric acid hydrochloride with 1-hydroxy-3-alkyl-6,6,9-trimethyl-7,8,9,10-tetrahydro-6H-dibenzo[b,d]pyran. The latter compounds can be made as described in Ghosh et al., J.Chem.Soc. 1940, pages 1121–1125 and in Adams et al., J.A.C.S. Vol. 62, pages 2405–2408. The hydrochloride salts can be converted to the corresponding free base by neutralization with an alkali.

The tetrahydrodibenzopyran compounds and their acid addition salts can be formulated with conventional ophthalmologically acceptable topical carriers for medicaments. In the form of their acid addition salts, they are sufficiently water-soluble so that they can be formulated by dissolving in an aqueous carrier, althouth it is preferred for best results that they be formulated by dispersing in an oleaginous carrier; in the form of the free bases they are water-insoluble and preferably are formulated in an oleaginous carrier. Suitable carriers may and preferably do include a compatible bacteriostat and/or an antioxidant as preservative(s) of the formulation in storage and use. Among suitable carriers are, in addition to aqueous media, mineral oil, petrolatum, vegetable oils such as peanut oil and sesame oil, and similar oleaginous materials. If desired, the oleaginous formulation can be dispersed in water or an aqueous medium to form an emulsion or dispersion. The preparation of such formulations is carried out under aseptic conditions to give a sterile product.

The tetrahydrodibenzopyran compounds which are the active agents can be employed in varying concentration in the carrier, from $10^{-4}\%$ to 10% or more by weight, preferably from 0.01% to 1%. The dose may also vary considerably, from 0.00003 mg. per kg. body weight to 3.3 mg/kg, preferably from 0.003 to 0.3 mg/kg, best results being obtained at a dosage level from 0.03 to 0.3 mg/kg.

EXAMPLES

There were combined with stirring in 55 ml of dry methylene chloride 0.82 g (3.18 mmoles) of 1-hydroxy-3,6,6,9-tetramethyl-7,8,9,10-tetrahydro-6H-dibenzo[b,d]pyran, 0.62 g (3.18 mmoles) of 4-diethylaminobutyric acid hydrochloride and 0.69 g (3.33 mmoles) of dicyclohexylcarbodiimide. After 16 hours it was found that some of the phenol was still present, as shown by TLC with 5% methyl alcohol in chloroform, and so there were added 31 mg of the acid hydrochloride and 35 mg of the carbodiimide and stirring at room temperature was continued for another 24 hours, when only a trace of the phenol remained.

The reaction mixture was cooled 5 hours in a refrigerator, the precipitate was separated by filtration and washed with 5 ml of methylene dichloride. The methylene chloride filtrate and wash liquid were combined, then evaporated and dried under vacuum for 15 minutes to leave a foam which was suspended in a mixture of 20 ml methylene chloride and 25 ml cyclohexane. The mix was left in a refrigerator overnight, filtered to remove the precipitate. The evaporation step was repeated and the foam was dissolved in a mixture of 5 ml of methylene chloride and 20 ml of dry ether from which crystals were obtained on scratching and cooling. The crystalline product, 1-[4-(diethylamino)butyryloxy]-3,6,6,9-tetramethyl-7,8,9,10-tetrahydro-6H-dibenzo[b,d]pyran hydrochloride, (the compound of I above in which R is methyl and $R_1$ and $R_2$ are ethyl), amounted to 1.263 g and melted at 150°–152° C., being identified as compound B in the tests which follow.

The corresponding free base, hereinafter called compound C, was formed by dissolving compound B in the minimum quantity of water, neutralizing it with dilute sodium bicarbonate solution, then extracting with ether. After drying the ether solution with sodium sulfate, the ether was evaporated and the residue, compound C, was subjected to 1 mm vacuum for 15 hours.

The hydrochloride product (B) and the free base (C) were each evaluated by topical application to the cornea of one eye of a conscious adult albino rabbit (wt. 2–4 kg) of either sex. The test formulation consisted of a solution in light mineral oil (Saybolt viscosity 125–135) containing in one case 0.1% and in another case 1.0% by weight of the active agent. One 50 microliter drop of the solution was applied to the 12 o'clock position and allowed to flow over the surface of the cornea of the right eye of each rabbit, and the intraocular pressure in both eyes of each rabbit was measured at hourly intervals after initial application using an Alcon Pneumotonograph which had been calibrated for rabbit eyes. Each measurement was made after application of a drop of tetracaine hydrochloride solution (0.5%) which was washed off after 5 to 10 seconds with at least 1 ml of saline solution. Four hours after the initial application of the mineral oil solution, the application was repeated.

There was employed as a control a mineral oil solution containing 0.1% by weight of $\Delta^9$-tetrahydrocannabinol. The results were as follows:

| Compound | | Maximum Fall in Intraocular Pressure Percent | Time to Maximum Fall, Minutes |
|---|---|---|---|
| Control (0.1%) | RE* | 16.8 ± 1.5 | 360 |
| | LE | 14.2 ± 1.8 | 360 |
| B (0.1%) | RE | 19.1 ± 1.9 | 240 |
| | LE | 17.4 ± 1.8 | 180 |
| C (0.1%) | RE | 15.0 ± 2.1 | 120 (remained at max. fall for 60 min.) |
| | LE | 12.8 ± 2.0 | 180 |
| C (1.0%) | RE | 13.3 ± 1.3 | 120 (remained at max. fall for 60 min.) |
| | LE | 14.2 ± 1.1 | 120 |

*RE = right eye; LE = left eye.

Tests of compound B (hydrochloride) in mice show it to have much less CNS activity than $\Delta^9$-tetrahydrocannabinol. Similar results can be obtained when there are substituted as the active agents other compounds having the structure I above, either the hydrochloride or other ophthalmologically acceptable acid addition salt or another free base, in which R, $R_1$ or $R_2$ is another alkyl group having 2 to 4 carbon atoms.

In general, the compounds of the present invention show a long duration of action, lasting from one hour to several hours.

What is claimed is:

1. The method of treating wide-angle glaucoma which comprises applying topically to the eye from 0.00003 to 3.3 mg/kg of body weight of a compound of the formula

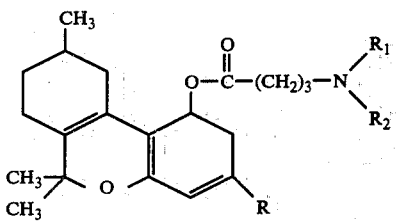

in which R, $R_1$ and $R_2$ are alkyl having from 1 to 4 carbon atoms or acid addition salts thereof.

2. The method as claimed in claim 1 in which R is methyl and $R_1$ and $R_2$ are ethyl.

3. The method as claimed in claim 2 in which the compound is the free base.

4. The method as claimed in claim 2 in which the compound is the hydrochloride.

* * * * *